United States Patent [19]

Bollen et al.

[11] Patent Number: 4,629,567

[45] Date of Patent: Dec. 16, 1986

[54] ALPHA-1-ANTIPROTEASE PURIFICATION

[75] Inventors: Alex J. Bollen, Itterbeek, Belgium; Paul Chuchana, Bordeaux, France; Marc Hoylaerts, Kessel-Lo, Belgium

[73] Assignee: SmithKline-RIT, Belgium

[21] Appl. No.: 836,868

[22] Filed: Mar. 7, 1986

[51] Int. Cl.$^4$ .............................................. B01D 15/08
[52] U.S. Cl. ................................... 210/635; 210/656; 210/690; 210/927; 435/815
[58] Field of Search ............... 210/635, 656, 663, 679, 210/690, 905, 908, 927; 435/213–215, 815; 436/161; 426/634

[56] References Cited

U.S. PATENT DOCUMENTS

| 3,808,124 | 4/1974 | Dziobkowski et al. | 210/690 |
| 4,205,130 | 5/1980 | Vihko | 435/815 |
| 4,264,449 | 4/1981 | Dodd | 210/656 |
| 4,525,465 | 6/1985 | Someno | 435/215 |
| 4,579,661 | 4/1986 | Gustafsson et al. | 210/635 |

OTHER PUBLICATIONS

Journal of Chromatography, 278, pp. 53–61, 1983.

*Primary Examiner*—John Adee
*Attorney, Agent, or Firm*—Edward T. Lentz; Janice E. Williams; Alan D. Lourie

[57] ABSTRACT

Alpha-1-antiprotease is highly purified from an impure solution thereof by a series of chromtographic procedures.

2 Claims, No Drawings

ALPHA-1-ANTIPROTEASE PURIFICATION

FIELD OF THE INVENTION

This invention relates to purification of human alpha-1-antiprotease, herein referred to as alpha-1-antitrypsin.

BACKGROUND INFORMATION

Alpha-1-antitrypsin (AAT) is an alpha-1-globulin present in serum and various other body fluids. As synthesized in the liver, mature AAT is a glycoprotein having a molecular weight of about 50,000 to 55,000 daltons. Proteolytic enzymes inhibited by AAT include trypsin, chymotrypsin, pancreatic elastase, skin collagenase, renin and urokinase, as well as proteases of polymorphonuclear lymphocytes. Genetically acquired deficiency of AAT in humans is associated with various pathological conditions, especially emphysema and liver disease. See, for example, Morse, *N. Eng. J. Med.* 299 (19):1045–1048 (1978) and 299 (20):1099–1105 (1978); Tobin et al., *Arch. Int. Med.* 143 (7):1342–1348 (1982); and Carrell et al., *Nature* 298 (5872):329–334 (1982).

Elastase is a proteinase which breaks down lung tissue. Unchecked, its activity can result in emphysema. Gadek et al., *Am. Rev. Respir. Dis.* 127:S45 (1983) and Glaser et al., Am. Rev. Respir. Dis. 127:547–553 (1983), for example, have shown that AAT can be therapeutically useful in treatment of emphysema.

Because of its therapeutic utility and because comparatively large amounts are required for certain indications, such as replacement therapy for patients genetically deficient in AAT, researchers have been looking for techniques to produce AAT in large quantities. Conventionally such techniques have involved purification of AAT from blood plasma.

Recent efforts have focused on production of AAT in transformed microorganisms or cells, especially *E. coli* and yeast, due to the promise of such techniques to produce large quantities of engineered gene products. Several researchers have reported success in such endeavors. However, a practical process for purifying such recombinant AAT is useful in pharmaceutical applications is not available.

It is an object of the present invention to provide an improved process for purifying AAT from serum or from recombinant microorganisms, yeasts or cells, especially from recombinant bacteria and yeasts, which is capable of performance at large scale.

Laurell et al., *J. Chromatog.* 278:53–61 (1983) describe use of thiol-disulfide exchange chromatography to isolate AAT.

SUMMARY OF THE INVENTION

The invention is a process for purifying AAT from an impure solution thereof which comprises:

(1) contacting the solution with an ion exchange adsorbent, and eluting the AAT therefrom;

(2) contacting the eluate from (1) with a thiol-disulfide exchange adsorbent and eluting the AAT therefrom;

(3) contacting the eluate from (2) with heparin bound to a solid carrier;

(4) contacting the effluent from (3) with a zinc-chelate adsorbent and eluting the AAT therefrom;

(5) contacting the eluate from (4) with an ion exchange adsorbent and eluting the AAT therefrom.

DETAILED DESCRIPTION OF THE INVENTION

The process of the invention comprises a series of adsorption steps each of which, individually, is carried out in accordance with standard techniques of protein purification. While the individual steps are, in a general sense, standard protein purification techniques, particular steps in a particular sequence must be selected from the myriad possibilities of process steps and sequences to achieve a purification process which is effective and efficient.

The AAT purified by the process of the invention can be identical to serum-derived AAT. The invention can also be applied to variant AAT molecules, that is, AAT molecules varying from natural AAT in secondary or tertiary structure, as may be the case for certain recombinant DNA-derived AAT proteins. Variant AAT molecules differing in primary structure can also be employed, provided that ability of the AAT to form disulfide bonds in the thioldisulfide exchange step is not significantly adversely affected. Useful variant AAT molecules include, for example, those disclosed by Courtney et al., EP-A No. 114,777, Courtney et al., *Nature* 313:149 (1985) and Bollen et al., *DNA* 2:255 (1983).

The steps in the process of the invention are preferably carried out as chromatography steps, that is, continuous flow through an adsorbent, rather than batch-wise. The adsorbents used in the process of the invention comprise a solid carrier matrix through which various AAT-containing solutions are passed, thereby contacting a ligand for adsorbing the AAT or one or more impurities. Known such solid carriers include glass, silica, alumina and zirconia as well as organic carriers such as agarose, cellulose, dextran, polyamide, polyacrylamide and vinyl copolymers of bifunctional acrylates with various hydroxylated monomers. Commercially available carriers include Aff-gel®, Sephadex®, HP resins such as HP-20, XAD resins, Sepharose® and others.

The process employs an impure solution of AAT, that is, a solution in which AAT is less than 25% pure and typically is less than 10–15% pure. Such solution can be, for example, serum, medium from a producing bacterial or other cell culture in which the AAT is secreted or an extract from a bacterial or yeast host in which the AAT is soluble. A crude bacterial or yeast extract is preferably partially purified such as by selective ammonium sulfate precipitation followed by resolubilization or selective precipitation of contaminating proteins such as by use of a polyalkyleneglycol. Techniques for preparing serum containing AAT are well-known. Techniques for preparing bacterial or other cell extracts containing soluble protein or for solubilizing protein in such extracts are also well-known. For example, *E. coli* transformants are collected by centrifugation and lysed for 30 min at 0° C. in one-tenth volume of TES buffer (50 mM Tris, pH 8, 5 mM EDTA and 25% sucrose) supplemented with 0.5 mg/ml of lysozyme and 10 mg/ml of DNAse. Triton X100 is then added to a final concentration of 0.1%. The suspension is incubated at 0° C. for 15 min and then brought to 80 mM $Mg^{++}$ by addition of 1M $MgCl_2$. This suspension is incubated for 5 min at 25° C. A supernatant is collected following centrifugation at 15,000 rpm for 10 min. Ammonium sulfate is added to the supernatant and the solution is centrifuged for 10 min at 10,000 rpm. The AAT is detected in the 50–75% ammonium sulfate fraction. This precipitate is resolubilized in buffer (50 mM Tris, pH 8, 25 mM NaCl) and dialyzed against the same buffer.

The first step in the process of the invention is an ion exchange step carried out in the presence of a mild detergent to remove lipids and most nucleic acids. An ion exchange column, preferably a DEAE column, such as DEAE-agarose, is equilibrated to approximately neutral pH, preferably 6.5, with a phosphate buffer containing a small amount of the detergent. After flowing the impure solution of AAT through the column, the column is washed with the equilibration buffer. Then the AAT is eluted with a salt, preferably about 150–250 mM NaCl in the equilibration buffer. The salt eluate is concentrated such as by filtration or dialysis. Ethylene diaminetetracetate (EDTA) is added to a final concentration of about 20 mM and the pH is raised to above neutral, e.g., >pH 7 to about pH 10, preferably pH 8–9.

In the second step, the concentrated eluate from step (1) is contacted with a thiol-disulfide exchange adsorbent. Such procedure utilizing immobilized human kappa (K) light chains is described by Laurell et al., *J. Chromatog.* 278:53–61 (1983). AAT is eluted from the K light chains bound to a solid carrier with a reducing agent, preferably 4-nitrophenyl-disulfide-3,3'-dicarbonic acid and/or beta-mercaptoethanol to disrupt the disulfide bonds. The eluate was concentrated, desalted and adjusted to pH 7–8.

The concentrated eluate from step (2) is then contacted with heparin bound to a solid carrier, such as a heparin-agarose column, at ionic strength to adsorb most residual lipoproteins. The flow-through, that is, the effluent, from this adsorbent contains the AAT.

In the fourth step, the effluent from the heparin step is contacted with immobilized $Zn^{2+}$ ions, such as a zinc-chelate column, preferably an agarose column, to selectively adsorb AAT. The AAT is eluted by lowering the pH to below 6, for example, 5.5, or by step-wise elution with histidine. Following acid elution, the pH is quickly readjusted to about neutral, that is, pH 6.5–7.5. The eluate is then dialyzed to remove eluting agents.

In the fifth step, the AAT solution is contacted with a second ion exchange adsorbent, preferably an aminohexyl agarose column. AAT is specifically eluted using a salt gradient (150–250 mM NaCl). Pure AAT eluant is desalted such as by dialysis and concentrated, preferably by lyophilization.

The AAT resulting from this procedure can, if desired, be subjected to further purification steps to remove trace contaminants such as by affinity chromatography employing, for example, immobilized anhydrochymotrypsin or immobilized antibodies to AAT or to protein contaminants.

EXAMPLES

The Examples which follow are illustrative, and not limited, of a preferred purification process of the invention.

EXAMPLE 1

Purification of Mature AAT from Yeast

Recombinant plasmids expressing mature human AAT under the control of the yeast arg3 promoter, as previously described by Cabezon et al., *Proc. Natl. Acad. Sci. USA* 81:6594–6598 (1984), were used to express AAT in peptidase-deficient *S. cerevisiae* strains 10S442 (leu2-3, leu2-112, pep4-3) and TCY1 (ura3, leu2 defective).

Preliminary Precipitation: After mechanical disruption of cell membranes of about 1.5 to 2 kg of yeast, in an ethanol-dry ice cooled Dyno-Mill at 3000 rpm (pumping speed around 5 l/h), in the presence of 20 mM n-mercaptoethanol, 5 mM EDTA, 1 mM PMSF and 1 mM benzamidine (total volume 2.0 to 2.5 l) in 50 mM Tris-HCl buffer, pH 8.0, the pH of the crude extract was adjusted to 6.5 with 1 N HCl under stirring. Solid polyethylene glycol 1000 was added to 7%. Upon two hours of incubation, this crude extract was centrifuged at 16,000 g for 5 hours. Precipitated yeast membranes (around 500 ml) were resuspended in b l 20 mM phosphate buffer pH 6.5, containing 7% PEG 1000 under sonication and recentrifuged for at least 5 h. Both supernatants were pooled (about 3), Triton WR1339 was added to 0.1%, and if necessary, the pH was adjusted to 6.5. Total ionic strength was measured and if necessary adjusted to 70 mM of NaCl equivalent units by dilution with distilled water.

DEAE-chromatography: The AAT (herein $\alpha_1$-PI) containing extract, partially depleted in cellular organelles and lipoproteins, was then charged onto a preparative DEAE-Sepharose Fast Flow column (5×26 cm) equilibrated in 20 mM phosphate buffer pH 6.5 containing 0.1% Triton and 0.01% $NaN_3$, at a flow rate of 600 ml/h. The column was washed with the starting buffer until the absorbance (280 nm) of the effluent fell below 2.0 (approximately 10 l), upon which an $\alpha_1$-PI containing protein fraction was eluted stepwise with 150 mM of NaCl, added to the starting buffer. Residual fixed compounds were stepwise eluted with 1M NaCl and 0.5M NaOH respectively, after which the column was reequilibrated with the starting buffer. Upon concentrating the $\alpha_1$-PI fraction to about 400 ml, EDTA was added to 20 mM and the pH was raised to 8.5 with solid Tris-powder.

Thiol-exchange chromatography: The slightly enriched material obtained in the previous step was applied onto a resin, consisting of human immunoglobulin light chains, idiotype K, insolubilized on sepharose 4B, following cyanogen bromide coupling. As previously indicated, human K-light chains can be isolated from urine of myeloma patients, subject to the Bence-Jones syndrome. Upon charging batches of concentrated urine onto DEAE-Sepharose columns, the K-chains were incubated with saturating concentrations of bis-(4-nitrophenyl)disulfide-3,3'-dicarbonic acid (DTNB) in 1M Tris-HCl buffer pH 8.5, containing 100 mM EDTA for four days at room temperature. This procedure effectively dissociated dimers, which appear upon formation of a disulfide bond between C-terminal cysteines present in the K-chains, and introduced a protective group from thiol-functions. After separation of the excess of DTNB and TNB by sephadex G-25 chromatography, the protected K-chains were linked to 500 ml of Sepharose 4B, activated with CNBr just prior to use. In this way 0.4 moles of thiols were introduced per ml of gel, as calculated from the absorbance (412 nm) of TNB detached from the resin upon complete reduction of disulfide bridges with $\beta$-mercaptoethanol ($\beta$-SH).

The $\alpha_1$-PI solution was passed through a column of insolubilized K-chains (2.6×94 cm), equilibrated in 50 mM Tris HCl buffer containing 200 mM NaCl, 20 mM EDTA, 0.1% Triton and 0.01% $NaN_3$, at a flow rate of 100 ml/h. The flow-through was treated with 20 mM β-SH to reduce disulfide bridges involving TNB and soluble proteins, and was dialysed against the chromatography buffer, to which active charcoal was added to accelerate elimination of TNB. This flow-through (not entirely depleted in α1-PI) subsequently was repassed onto the column as described for the first passage.

After each passage, the column was washed with the starting buffer and protein fractions containing α1-PI was specifically eluted with an excess of TNB (1 mg/ml of DTNB+0.25 mg/ml of dithiothreitol in the starting buffer), which reverses the equilibrium

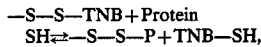
—S—S—TNB+Protein
SH⇌—S—S—P+TNB—SH, and hence detaches some proteins, amongst which is α1-PI.

A total elution was subsequently realized through complete reduction of disulfide bridges with 20 mM β-SH added to the starting buffer. Prior to use, the column was reactivated by passing 1 mg/ml of DTNB in the starting buffer.

The specifically eluted α1-PI containing fraction was reduced with 20 mM β-SH and dialysed against 20 mM phosphate buffer pH 7.5, to which active charcoal was added.

Alternatively upon reduction, the eluate was concentrated in an Amicon DC2 concentrator to 150 ml and desalted by sephadex G-25 chromatography in a column (5×50 cm) equilibrated with 20 mM phosphate buffer pH 7.5.

Heparin-agarose-chromatography: the dialysate of chromatographically desalted α1-PI solution was applied onto an heparin-agarose column (2.6×36 cm) equilibrated in 20 mM phosphate buffer pH 7.5 and washed with the starting buffer at a flow rate of 70 ml/h. The flow-through of this step was pooled and subsequently used. Proteins bound to the column were eluted with 1M NaCl and discarded. Every fifth cycle, a solution of 2M NaSCN was passed to detach molecules sticking to the agarose by non-specific interactions.

Zn-chelate-chromatography: The flow-through of the preceding step was deposited either as a pool of collected fractions, either directly by connecting the outlet of the heparin-agarose column to the inlet of a column of chelating sepharose (2.6×19 cm) charged with $Zn^{2+}$-ions, and equilibrated with 20 mM phosphate buffer pH 7.5. After completely charging the column, it was washed with 25 mM phosphate buffer pH 6.5, containing 0.5M NaCl. Specific elution of principally α1-PI was obtained upon lowering the pH to 5.5 or by gradient elution with histidine (0–25 mM) in the wash buffer. It was followed by a non-selective elution with 50 mM EDTA in 0.2 M Tris-HCl buffer pH 8.0, upon which the column was reequilibrated with $ZnCl_2$. In case of acid elution, the pH was raised immediately to about 7 by 1 ml of 1 M Tris HCl buffer pH 8.0, present in the tubes during collection of the eluate. The pooled eluate was subsequently dialysed against 25 mM phosphate buffer pH 6.5, 25 mM NaCl.

AH-Sepharose chromatography: The α1-PI solution, still slightly contaminated, is charged onto an aminohexyl agarose column (2.6×18 cm) (AH-Sepharose, Pharmacia, Stockholm, Sweden) used as an ion-exchanger and equilibrated in 25 mM phosphate buffer pH 6.5, 25 mM NaCl. Adsorbed proteins were eluted by a total volume of 600 ml of a linear gradient of NaCl (25 to 300 mM) in the starting buffer, at a flow rate of 50 ml/h. Pure α1-PI containing fractions were pooled and dialysed against 5 mM phosphate buffer pH 7, 15 mM NaCl and lyophilised. Upon dissolving the purified α1-PI in one-tenth of the initial volume before lyophilisation in distilled water, ten-fold concentrated samples were obtained, having an adequate ionic strength for preservation of biological activity.

EXAMPLE 2

Purification and Activity of Various AAT Molecules

The following AAT molecules were purified substantially by the procedure described in Example 1:

1. AAT deleted in 5 N-terminal amino acids and expressed in *E. coli;*
2. mature AAT (having N-met in place of the N-glu and lacking the ala at position 8) expressed in *E. coli;*
3. mature AAT (having N-met in place of the N-glu) expressed in yeast;
4. AAT from human plasma.

*E. coli* transformants were lysed to prepare cell extracts from which AAT was precipitated with ammonium sulfate substantially as described in the specification, above.

AAT was derived from plasma by standard techniques.

The activity of the four AAT proteins purified by the method of the invention was compared to that of a standard AAT preparation derived from serum in a standard trypsin inhibition assay. The assay measures the inhibitory capacity of α1-antitrypsin toward trypsin. It consists of a microtest using the chromogenic substrate S2444 (L-pyroglutamylglycyl-L-arginine, p-nitroanilide hydrochloride, Kabi Diagnostica, Stockholm, Sweden). The polystyrene microtest plates were incubated for 1 hr with 1% bovine serum albumin and washed extensively with distilled water. α1-antitrypsin at various concentrations was incubated with a fixed amount of trypsin for 20 min at 37° C. in a 200- 1 final reaction volume of 0.1 M Tris-HCl pH 8.2/0.15 M NaCl/0.01 M EDTA/0.5% polyethylene glycol, $M_r$6000). Samples were cooled slowly at room temperature and then exposed to the chromogenic substrate (20 μl of aqueous solution of 0.003 M S2444). After 5 min at room temperature, the reaction was stopped with 50 μl of 50% acetic acid.

Absorbance was read at 405 nm in a micro-ELISA automatic reader (Dynatech AM120). Calibration curves were determined for both trypsin and α1-antitrypsin. Samples to be assayed were diluted serially in reaction buffer.

The results, which are reported in the following table, demonstrate that the process of the invention can be used to purify AAT from various sources, including variant AAT molecules, without adversely affecting the protease-inhibiting activity thereof. Samples 1, 2, 3 and 4 are as defined above.

| AAT concentration (ug/ml) | Activity assay of purified AAT produced in microorganisms or derived from pooled human plasma | | | | |
|---|---|---|---|---|---|
| | Optical density ($A_{410}$) (inhibition of trypsin activity) | | | | |
| | standard | 1 | 2 | 3 | 4 |
| 0 | .95(0) | 1.00(0) | 1.02(0) | 1.02(0) | 0.90(0) |
| 0.25 | — | 0.56(44) | — | 0.95(7) | 0.74(17) |
| 0.50 | .78(11) | 0.16(84) | 0.9(10) | 0.84(17) | — |
| 1 | .63(33) | 0.05(95) | — | — | 0.48(46) |
| 1.50 | — | — | 0.47(54) | 0.54(47) | — |

Activity assay of purified AAT produced in microorganisms or derived from pooled human plasma -continued

| AAT concentration (ug/ml) | Optical density ($A_{410}$) (inhibition of trypsin activity) | | | | |
|---|---|---|---|---|---|
| | standard | 1 | 2 | 3 | 4 |
| 2 | .32(66) | — | — | — | 0.06(93) |
| 2.50 | .24(74) | | | | |
| 3.50 | .17(82) | | | | |
| 4.50 | .1(90) | | | | |

% inhibition of trypsin activity is shown in parentheses

The above description and examples fully disclose the subject invention including the preferred embodiments thereof. The invention, however, is not limited to the precise construction described therein but, rather includes all modifications and variations thereof which are encompassed within the scope of the claims which follow.

We claim:

1. A process for purifying alpha-1-antitrypsin from an impure solution thereof which comprises:

(1) contacting the solution with an ion exchange adsorbent, and eluting the alpha-1-antitrypsin therefrom;

(2) contacting the eluate from (1) with a thiol-disulfide exchange adsorbent and eluting the alpha-1-antitrypsin therefrom;

(3) contacting the eluate from (2) with heparin bound to a solid carrier;

(4) contacting the effluent from (3) with a zinc-chelate adsorbent and eluting the alpha-1-antitrypsin therefrom;

(5) contacting the eluate from (4) with an ion exchange adsorbent and eluting the alpha-1-antitrypsin therefrom.

2. The process of claim 1 in which each step is carried out in chromatographic fashion and which comprises, in step (1), contacting the solution with a DEAE ion-exchange column in the presence of a detergent, and eluting the alpha-1-antitrypsin therefrom with 150–250 mM NaCl;

in step (2), contacting the eluate from (1) with an immobilized human K light chain column and eluting the alpha-1-antitrypsin therefrom with a reducing agent;

in step (4), contacting the effluent from (3) with a Zn-chelate column and eluting the alpha-1-antitrypsin therefrom by lowering the pH to less than 6 or by contacting the bound alpha-1-antitrypsin with histidine and immediately adjusting the pH to 6.5–7.5; and, in step (5), contacting the eluate from (3) with an amino-hexyl ion exchange column and eluting the alpha-1-antitrypsin therefrom with NaCl (150 mM to 250 mM).

* * * * *